(12) United States Patent
Hou et al.

(10) Patent No.: US 12,178,995 B2
(45) Date of Patent: Dec. 31, 2024

(54) INFUSION HEIGHT WARNING AND BLOCKING DEVICE, AND INFUSION HEIGHT WARNING AND BLOCKING METHOD THEREOF

(71) Applicant: Wistron Corporation, New Taipei (TW)

(72) Inventors: Chia-Chang Hou, New Taipei (TW); Yi-Sheng Kao, New Taipei (TW)

(73) Assignee: Wistron Corporation, New Taipei (TW)

(*) Notice: Subject to any disclaimer, the term of this patent is extended or adjusted under 35 U.S.C. 154(b) by 345 days.

(21) Appl. No.: 17/203,779

(22) Filed: Mar. 17, 2021

(65) Prior Publication Data

US 2022/0233769 A1 Jul. 28, 2022

(30) Foreign Application Priority Data

Jan. 28, 2021 (TW) ................. 110103286

(51) Int. Cl.
 *A61M 5/14* (2006.01)
 *A61M 5/168* (2006.01)

(52) U.S. Cl.
 CPC ...... *A61M 5/16818* (2013.01); *A61M 5/1415* (2013.01); *A61M 2205/18* (2013.01); *A61M 2205/3334* (2013.01)

(58) Field of Classification Search
 CPC ........ A61M 5/1723; A61M 2005/1726; A61M 2205/33; A61M 2230/005; A61M 5/14; A61M 2005/1416; A61M 2005/1401; A61M 5/168; A61M 5/16804; A61M 5/16881; A61M 5/16886; A61M 2205/3331; A61M 2205/3379; A61M 2205/35; A61M 2205/50; A61M 2209/08; A61M 2209/084; A61M 2209/088
See application file for complete search history.

(56) References Cited

U.S. PATENT DOCUMENTS

| | | | |
|---|---|---|---|
| 2012/0116348 A1* | 5/2012 | Katoh | A61M 5/14224 604/67 |
| 2016/0051750 A1* | 2/2016 | Tsoukalis | A61M 5/16813 235/375 |
| 2018/0050152 A1* | 2/2018 | Kuo | A61M 5/1689 |
| 2019/0001057 A1* | 1/2019 | Tsoukalis | G06K 7/10366 |
| 2021/0401670 A1* | 12/2021 | Abal | A61M 5/1414 |
| 2022/0118178 A1* | 4/2022 | Carlisle | G16H 20/17 |

FOREIGN PATENT DOCUMENTS

| | | |
|---|---|---|
| CN | 104969227 A | 10/2015 |
| CN | 106964023 A | 7/2017 |
| CN | 107754053 A | 3/2018 |

\* cited by examiner

*Primary Examiner* — Shefali D Patel
*Assistant Examiner* — William R Frehe
(74) *Attorney, Agent, or Firm* — Winston Hsu (57) ABSTRACT

An infusion height warning and blocking device for an infusion stand is provided. The infusion height warning and blocking device includes a communication module for receiving at least one sensing signal from at least one gravity sensor; and a processing unit for calculating an infusion height difference between a start position and a usage position according to the at least one sensing signal, and generating at least one height indication signal according to the infusion height difference and at least one height difference threshold.

20 Claims, 6 Drawing Sheets

INFUSION HEIGHT WARNING AND BLOCKING DEVICE, AND INFUSION HEIGHT WARNING AND BLOCKING METHOD THEREOF

BACKGROUND OF THE INVENTION

1. Field of the Invention

The present invention relates to an infusion height warning and blocking device and infusion height warning and blocking method thereof, and more particularly, to an infusion height warning and blocking device and infusion height warning and blocking method thereof capable of utilizing gravity sensors to accurately determine an infusion height difference, and effectively performing different operations for different infusion height differences to maintain a flow rate and avoid a backflow or an excessive flow rate.

2. Description of the Prior Art

For an infusion device commonly used in medical procedures (such as drips), when a patient is being administered, a height difference between the hand or the arm position and the infusion bottle is less than a certain distance (such as less than 75 to 90 cm) because the needle in the blood vessel makes the patient uncomfortable or the patient moves (to the toilet or walking) with the infusion stand, which will cause the infusion flow rate to slow down, the infusion tube blocked, and even the venous blood backflow. This will not only easily cause the infusion process to be unsmooth, but also require nursing staffs to change the needle and increase patient discomfort.

To solve the above problems, the conventional technology uses radio-frequency signals combined with semi-obstructing metal structure as a solution. The principle is that after the patient's hand is higher than a certain height, the radio-frequency signal from the hand may be above the semi-obstructing metal structure and may be received by the radio-frequency receiver behind to determine that the hand is too high. However, the conventional method lacks a two-stage operation of first warning and then blocking and is not flexible. Besides, it is not easy to block the radio-frequency signal in practical applications. Even if the semi-obstructing metal structure is used to block the radio-frequency signal in specific directions, it is still easy for the receiver to receive the radio-frequency signal after multiple reflections. Therefore, even though there is sufficient high difference between the infusion position and the infusion bottle, the receiver still receives the reflected radio-frequency signal from other directions to cause a false alarm.

Therefore, it is necessary to improve the prior art.

SUMMARY OF THE INVENTION

It is therefore an objective of the present invention to provide an infusion height warning and blocking device and infusion height warning and blocking method thereof capable of utilizing gravity sensors to accurately determine an infusion height difference, and effectively performing different operations for different infusion height differences to maintain a flow rate and avoid a backflow or an excessive flow rate.

The present invention discloses an infusion height warning and blocking device for an infusion stand is provided. The infusion height warning and blocking device includes a communication module for receiving at least one sensing signal from at least one gravity sensor; and a processing unit for calculating an infusion height difference between a start position and a usage position according to the at least one sensing signal, and generating at least one height indication signal according to the infusion height difference and at least one height difference threshold.

The present invention further discloses an infusion height warning and blocking method for an infusion stand. The infusion height warning and blocking method includes receiving at least one sensing signal from at least one gravity sensor; calculating an infusion height difference between a start position and a usage position according to the at least one sensing signal; and generating at least one height indication signal according to the infusion height difference and at least one height difference threshold.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
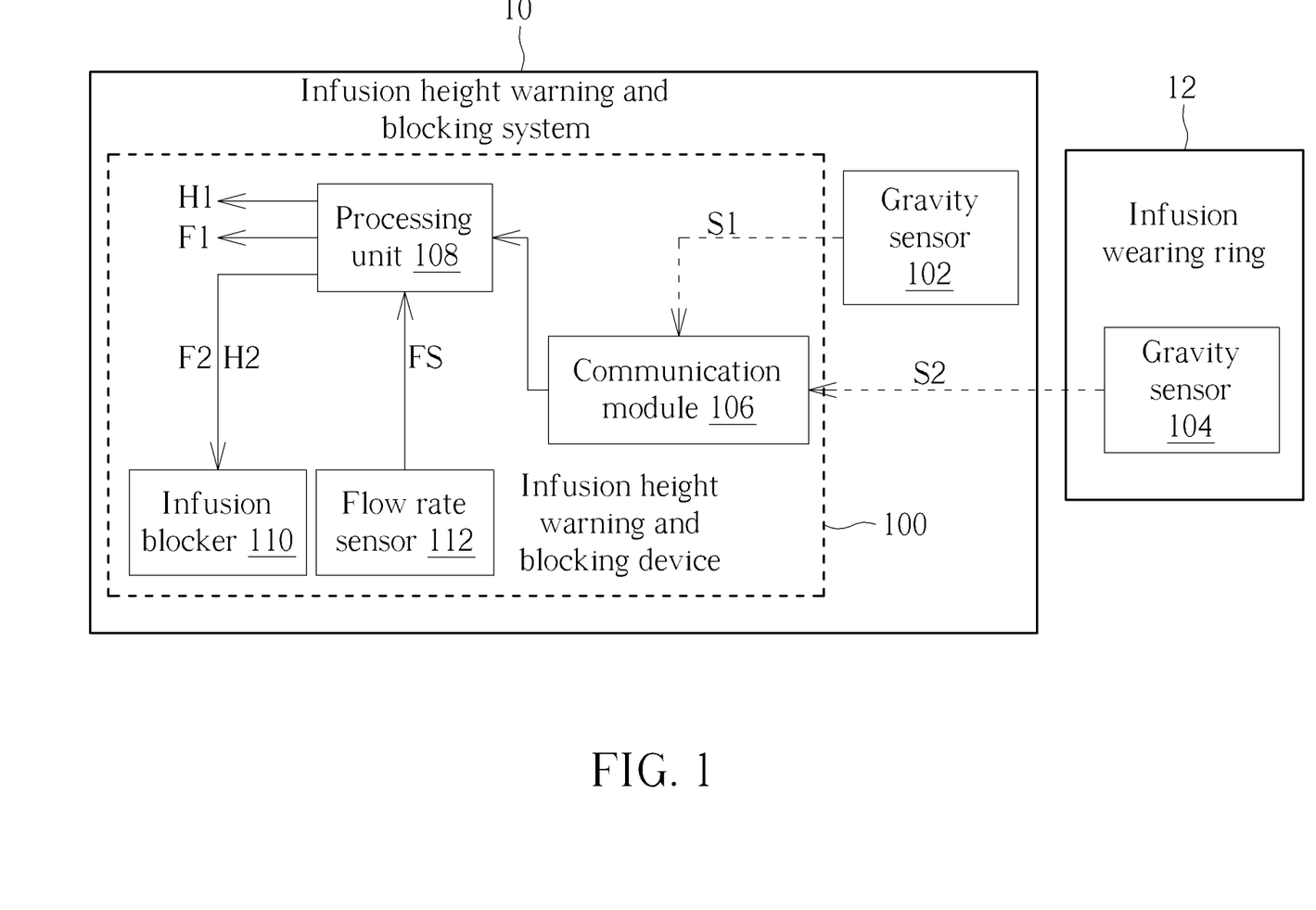
FIG. 1 is a schematic diagram of an infusion height warning and blocking system and an infusion wearing ring according to an embodiment of the present invention.

Please refer to FIG. 1, which is a schematic diagram of an infusion height warning and blocking system 10 and an infusion wearing ring 12 according to an embodiment of the present invention. As shown in FIG. 1, the infusion height warning and blocking system 10 includes an infusion height warning and blocking device 100 and at least one gravity sensor 102, 104. The infusion height warning and blocking device 100 is used for an infusion stand, and includes a communication module 106, a processing unit 108, an infusion blocker 110, and a flow rate sensor 112. In short, the gravity sensors 102, 104 detect information such as acceleration, gravity direction, time, etc. to generate at least one sensing signal S1, S2. The communication module 106 may receive the sensing signals S1, S2 from the gravity sensors 102, 104 (e.g., via wireless transmission such as blue tooth and WiFi, or through wired transmission). The processing unit 108 calculates an infusion height difference between a start position (e.g., an outlet of an infusion bottle disposed on an infusion stand) and a usage position (around a position of the infusion wearing ring 12) according to the sensing signals S1, S2, and generates at least one height indication signal H1, H2 according to the infusion height difference and at least one height difference threshold.

In detail, in response to the infusion height difference being smaller than a first height difference threshold (such as 75 to 90 cm) of the at least one height difference threshold, the processing unit 108 may generate the height indication signal H1 for warning (such as warning of insufficient vertical distance via a sound or light signal), so that a patient or a nursing staff may increase the height difference to maintain the flow rate. Furthermore, in response to the infusion height difference being less than a second height difference threshold (e.g. 10 cm) of the at least one height difference threshold or greater than a third height difference threshold (e.g. 100 cm) of the at least one height difference threshold, the processing unit 108 generates the height indication signal H2 to instruct the infusion blocker 110 to block an infusion tube to stop infusion (the infusion blocker 110 may be a mechanical clamping device for clamping and blocking flow of liquid in the infusion tube), to avoid obstruction, backflow or excessive flow rate (causing overloading on the patient's heart). As a result, the present invention accurately determines the infusion height difference between the start position and the usage position according to the sensing signals S1, S2 generated by the gravity sensors 102, 104, and effectively performs different operations for different infusion height differences to maintain a flow rate and avoid a backflow or an excessive flow rate.

On the other hand, the flow rate sensor 112 detects a current flow rate of an infusion tube (e.g., the flow rate sensor 112 is clamped on the infusion tube, and detects and calculates the flow rate by non-contact methods such as ultrasonic waves), to generate a flow rate sensing signal FS, and the processing unit 108 generates at least one flow rate indication signal F1, F2 according to the flow rate sensing signal FS and at least one flow rate threshold. In this case, in response to the current flow rate being greater or less than a first flow rate threshold of the at least one flow rate threshold by a specific ratio (such as greater than or less than a base flow rate in the initial infusion by 25%), the processing unit 108 may generate the flow rate indication signal F1 for warning (such as warning of the abnormal infusion rate via a sound or light signal), such that the patient or nursing staff may increase or decrease the height difference or adjust the infusion tube (e.g., unwinding or unbending) to maintain the flow rate. Furthermore, in response to the current flow rate being less than a second flow rate threshold of the at least one flow rate threshold (such as the current flow rate is 0 or backflow), the processing unit 108 generates the flow rate indication signal F2 to instruct the infusion blocker 110 to block the infusion tube to stop infusion (the infusion blocker 110 may be a mechanical clamping device for clamping and blocking flow of liquid in the infusion tube), to avoid obstruction and backflow. In this way, the present invention may accurately determine the current flow rate of the infusion tube according to the flow rate sensing signal FS generated by the flow rate sensor 112, and effectively perform different operations for different current flow rates, to maintain the flow rate and avoid obstruction and backflow.

Figure 2:
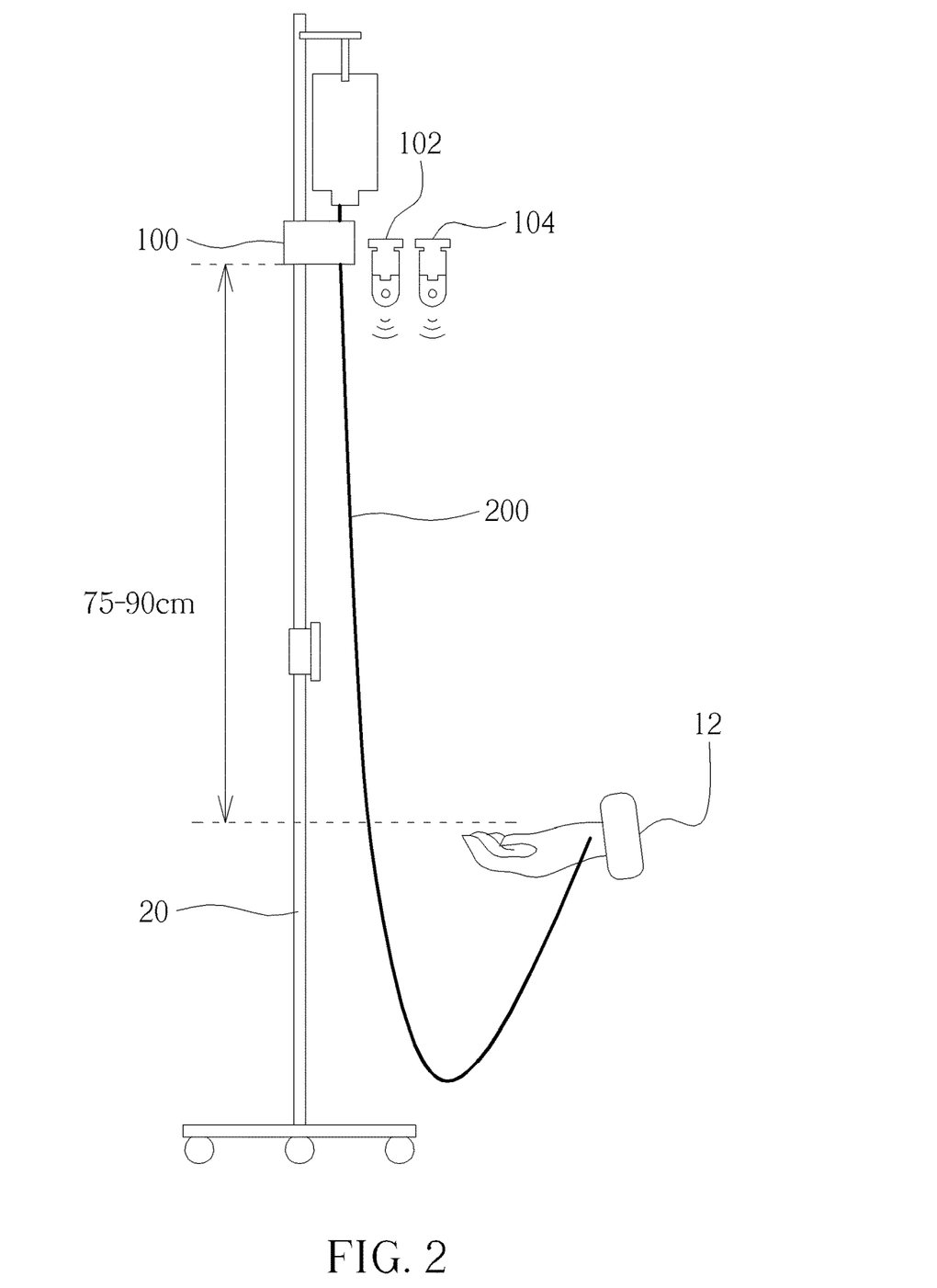
FIG. 2 to FIG. 4 are schematic diagrams of operations of the infusion height warning and blocking system and the infusion wearing ring shown in FIG. 1 utilized for an infusion stand according to an embodiment of the present invention.
Figure 3:
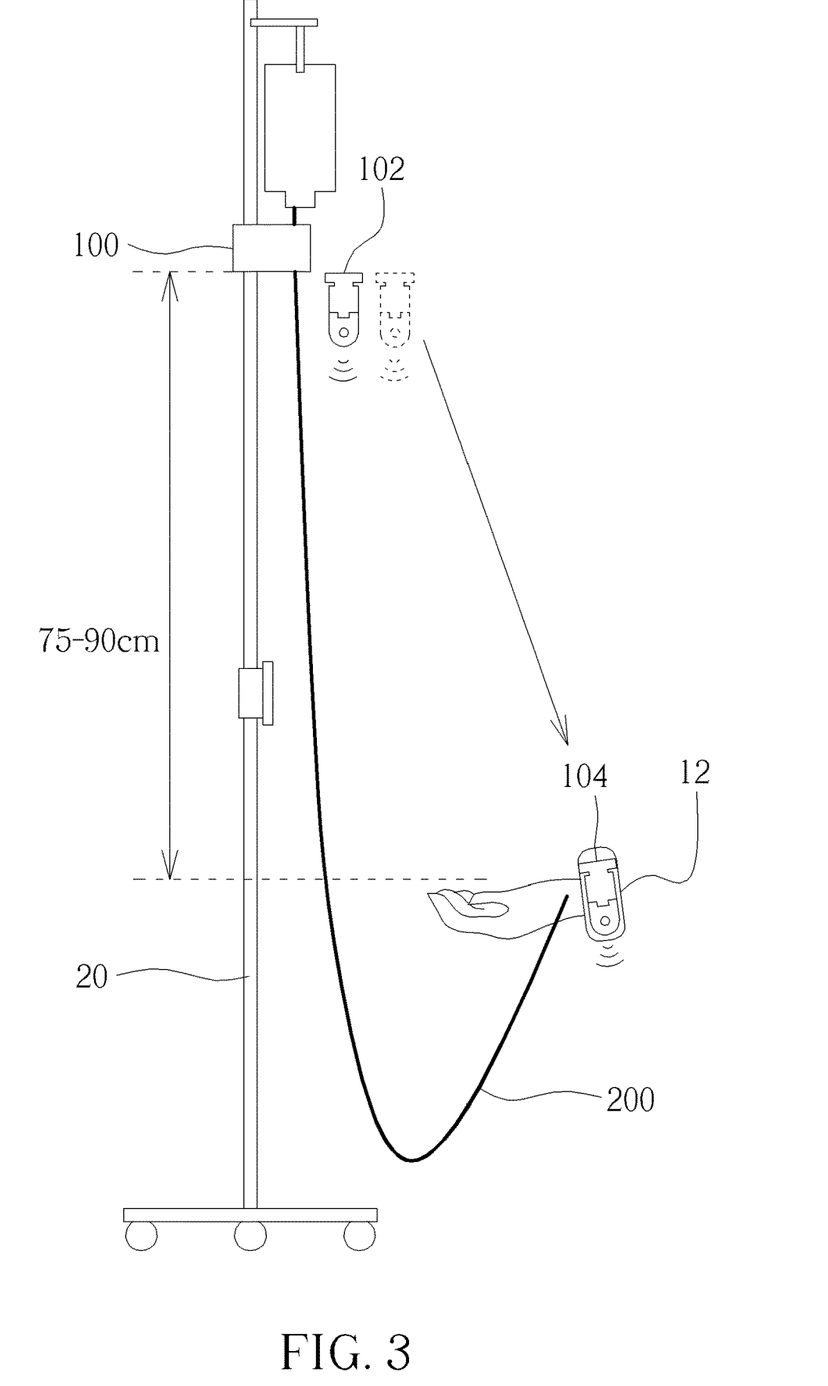
Figure 4:
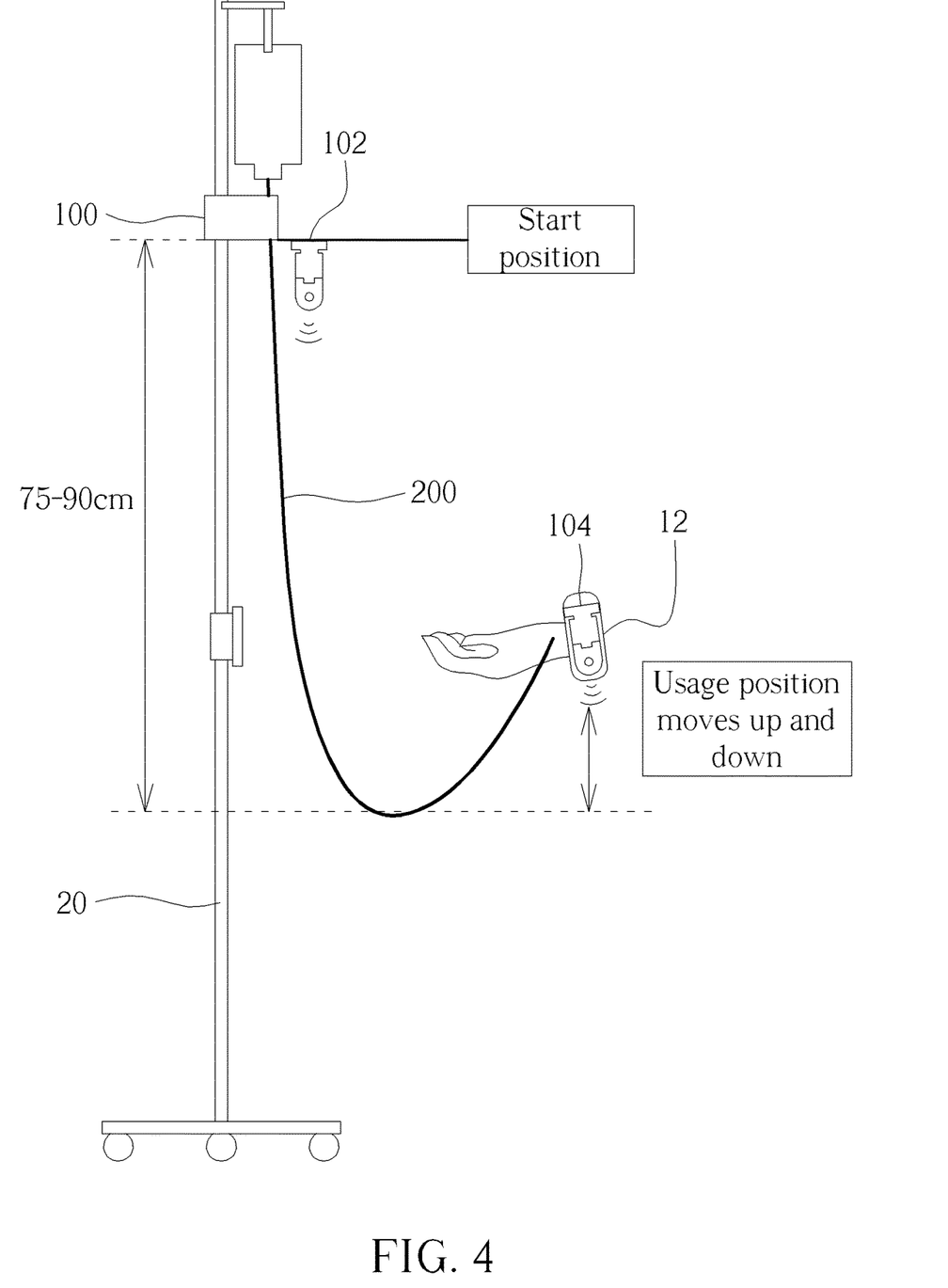

Specifically, refer to FIG. 2 to FIG. 4, which are schematic diagrams of operations of the infusion height warning and blocking system 10 and the infusion wearing ring 12 utilized for an infusion stand 20 according to an embodiment of the present invention. First, a nursing staff performs the infusion injection for the patient according to the general operation method (the vertical distance between the infusion bottle and the infusion part of the patient is about 75 to 90 cm), and completes the necessary adjustment of the flow rate during the infusion. Next, as shown in FIG. 2, the infusion wearing ring 12 is worn on the infusion part of the patient, and an infusion tube 200 is clamped with the infusion height warning and blocking device 100. At this time, the infusion tube 200 will pass the infusion blocker 110 and the flow sensor 112, and the flow sensor 112 may detect the current flow rate of the infusion tube 200 for the processing unit 108 to set as a base flow rate. Continue to FIG. 3. After the gravity sensor 104 is removed from the start position (other embodiments may remove the gravity sensor 102), the gravity sensor 104 continuously transmits the sensing signal S2 (generated by detecting acceleration data) to the processing unit 108. Thus, when the gravity sensor 104 is disposed at a usage position of the infusion wearing ring 12, the processing unit 108 may continuously calculate the infusion height difference between the start position and the usage position according to the sensing signal S2. The infusion height warning and blocking device 100 may charge the gravity sensors 102 and 104 at the start position, so that the gravity sensor 104 may continue to transmit the sensing signal S2 when removed from the start position and stopped being charged.

In this case, as shown in FIG. 4, when the patient acts or moves with infusion stand 20 and thus the usage position moves vertically, since the gravity sensor 104 continuously transmits the sensing signal S2 to the processing unit 108 and the processing unit 108 continuously calculates the infusion height difference between the start position and the usage position, the processing unit 108 may warn the insufficiency of the vertical distance through a sound or light in response to the infusion height difference being less than 75 to 90 cm, so that the patient or a nursing staff may increase the height difference to maintain the flow rate. In addition, in response to the infusion height difference being less than 10 cm or greater than 100 cm, the processing unit 108 may instruct the infusion blocker 110 to block the infusion tube 200 to stop the infusion, so as to avoid obstruction, backflow or excessive flow rate. Then, after the problem is solved and the infusion height difference is greater than 10 cm and less than 100 cm, the processing unit 108 may instruct the infusion blocker 110 to stop blocking the infusion tube 200 to restart the infusion.

On the other hand, in response to the current flow rate in the infusion tube 200 being greater than or less than the base flow rate by 25% (or other particular ratios), the processing unit 108 may warn the abnormal infusion rate via a sound or light signal, so that the patient or a nursing staff may increase or decrease the height difference or adjust the infusion tube 200 (such as unwinding or unbending) to maintain the flow rate. In addition, in response to the current flow rate being 0 or backflow, the processing unit 108 may instruct the infusion blocker 110 to block the infusion tube 200 to stop the infusion, so as to avoid obstruction, backflow or excessive flow rate. Noticeably, when the processing unit 108 does not warn that the vertical distance is insufficient or the infusion height difference is not less than 10 cm through a sound or a light signal, if the processing unit 108 determines that the current flow rate is 0 or backflow, and instructs the infusion blocker 110 to block the infusion tube 200, it means that the current problem about the flow rate is not caused by insufficient infusion height difference (probably due to winding or bending of the infusion tube 200), and requires nursing staffs to check conditions of the infusion tube 200 to solve the current problem about the flow rate. After that, when the problem is solved and the flow rate becomes normal, the infusion blocker 110 stops blocking the infusion tube 200 to restart the infusion, and the gravity sensor 104 does not need to return to the start position for reset.

It is worth noting that the above-mentioned embodiment mainly accurately determines the infusion height difference between the start position and the usage position according to the sensing signals S1 and S2 generated by the gravity sensors 102, 104, and effectively performs different operations for different infusion height differences to maintain the flow rate and avoid backflow or excessive flow rate. Those skilled in the art may make modifications or alterations accordingly, which are not limited to this. For example, in the above embodiment, since the infusion stand 20 may have a vertical height adjustment feature such that the start position is adjustable, although the patient does not move and the usage position is fixed, the gravity sensor 102 disposed at the start position may move up and down with adjustment of the infusion stand 20. Thus, the gravity sensor 102 may return the sensing signal S1 related to the acceleration information to the processing unit 108, and the processing unit 108 calculates the infusion height difference between the start position and the usage position by taking height adjustment of the infusion stand 20 into consideration with original vertical distance between the infusion bottle and the infusion part. In other embodiments, when the height of the infusion stand 20 is not adjusted and the start position is fixed, since the gravity sensor 104 is first disposed at the start position and then disposed at the usage position, the processing unit 108 may calculate the infusion height difference between the start position and the usage position only according to the sensing signal S2 (that is, only the gravity sensor 104 is required in this embodiment, but in practice, since the height of the infusion stand 20 is often adjusted and the gravity sensors 102 and 104 are often used alternately and are charged via the infusion height warning and blocking device 100, two gravity sensors 102 and 104 are usually disposed).

Figure 5:
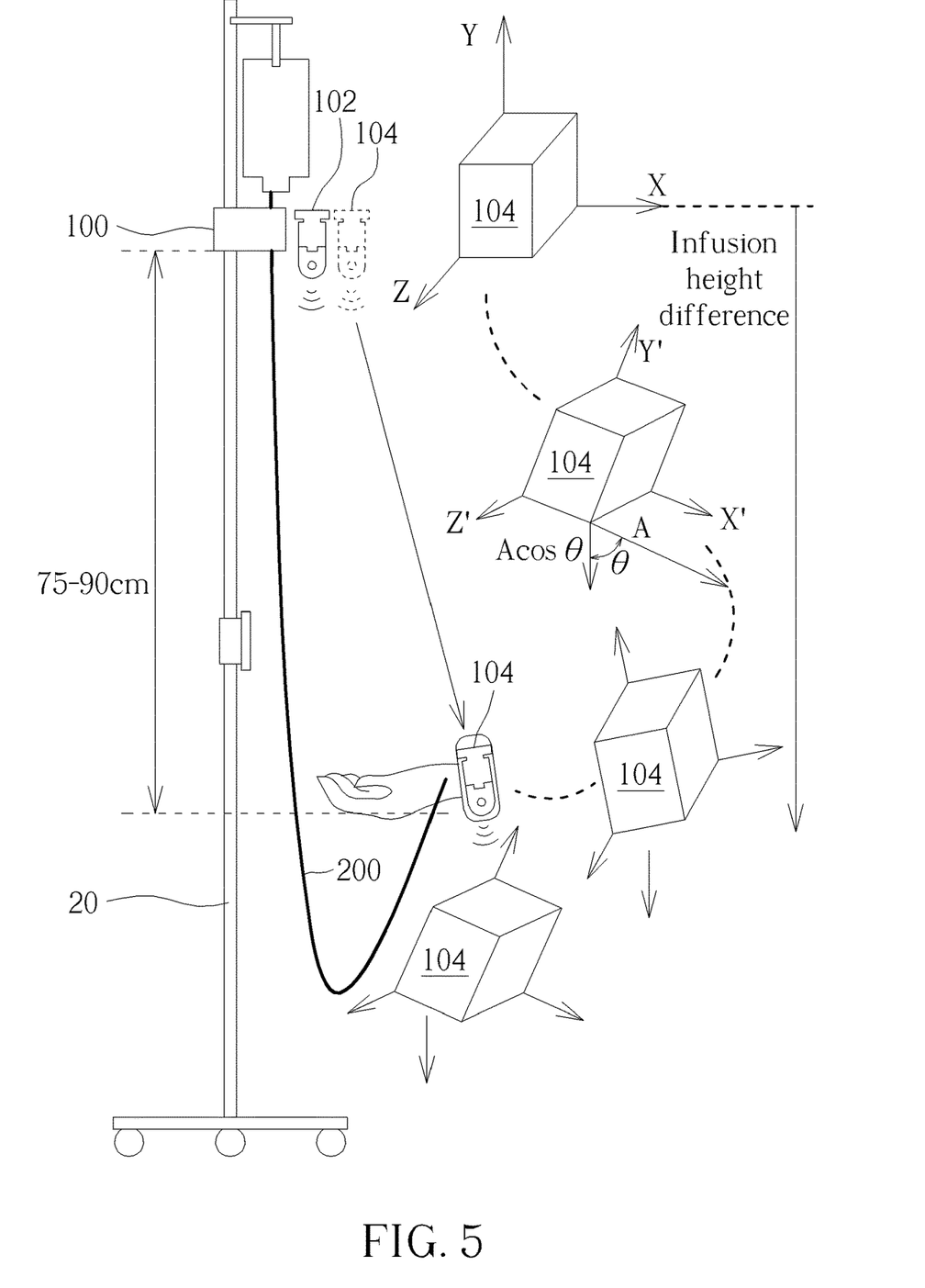
FIG. 5 is a schematic diagram of a processing unit calculating an infusion height difference when a gravity sensor performs operation shown in FIG. 3 according to an embodiment of the present invention.

In addition, please refer to FIG. 5, which is a schematic diagram of the processing unit 108 calculating an infusion height difference when the gravity sensor 104 performs operation shown in FIG. 3 according to an embodiment of the present invention. As shown in FIG. 5, when the gravity sensor 104 is removed from the start position, the gravity sensor 104 continues receiving force and transmitting the sensed signal S2 (generated by detecting acceleration data) to the processing unit 108. The processing unit 108 calculates the infusion height difference according to a vertical acceleration indicated by the sensing signal S2 during the moving process of the gravity sensor 104 (in other embodiments, if the position of the gravity sensor 102 also changes, another vertical acceleration indicated by the sensing signal S1 needs to be considered together). For example, when the gravity sensor 104 receives force and is changed from initial axes X, Y, and Z to axes X', Y', Z', the gravity sensor 104 may detect having an acceleration A and the acceleration A has an angle $\theta$ to the vertical direction to the ground, so that the vertical acceleration is $A \cos \theta$. The processing unit 108 obtains vertical displacement during the acceleration A from a relation $\frac{1}{2} A \cos \theta t^2$. By the same token, the processing unit 108 may add up respective vertical displacements of respective vertical accelerations during the moving process to obtain the infusion height difference.

In this case, please refer to FIG. 4 and FIG. 5 together. The gravity sensor 104 is disposed on the usage position of the infusion wearing ring 12, such as the wrist. Since the arm length of an adult is about 1 meter (m), when the patient acts to cause the usage position to move up and down as shown in FIG. 4, the movement may be considered as an arc with an arm as a radius, for example, when the arm is from a flat position to the highest point and then back to the flat position (i.e. 90-degree arc to and fro), the moving distance is 2*2*3.14*1/4=3.14 meters. If the frequency of the above-mentioned 90-degree arc to and fro is 60 times per minute (that is, 1 time per second), then the moving is 3.14 meters per second. As a result, under a situation that an interval between each data of the sensing signal S2 generated by the gravity sensor 104 is 1 ms, the gravity sensor 104 equivalently generates each data of the sensing signal S2 when moving 3.14 mm. In the application of the infusion stand 20, the processing unit 108 has enough data to determine the movement status of the gravity sensor 104, and may add up the vertical displacements to obtain the infusion height difference when the patient moves up and down as shown in FIG. 4. By the same token, the processing unit 108 also has sufficient amount data to add up the vertical displacements to obtain the infusion height difference when the gravity sensor 104 is removed from the start position and then disposed at the usage position as shown in FIG. 5. In some embodiments, a sampling frequency of the sensing signal S2 may be adjusted according to requirements of calculation amount and sensing sensitivity. For example, the interval between each data of the sensing signal S2 generated by the gravity sensor 104 may be adjusted to 4 ms, in order to reduce calculation amount of the processing unit 108; or, the interval between each data of the sensing signal S2 generated by the gravity sensor 104 may be adjusted to 0.25 ms, to improve the sensing sensitivity.

Figure 6:
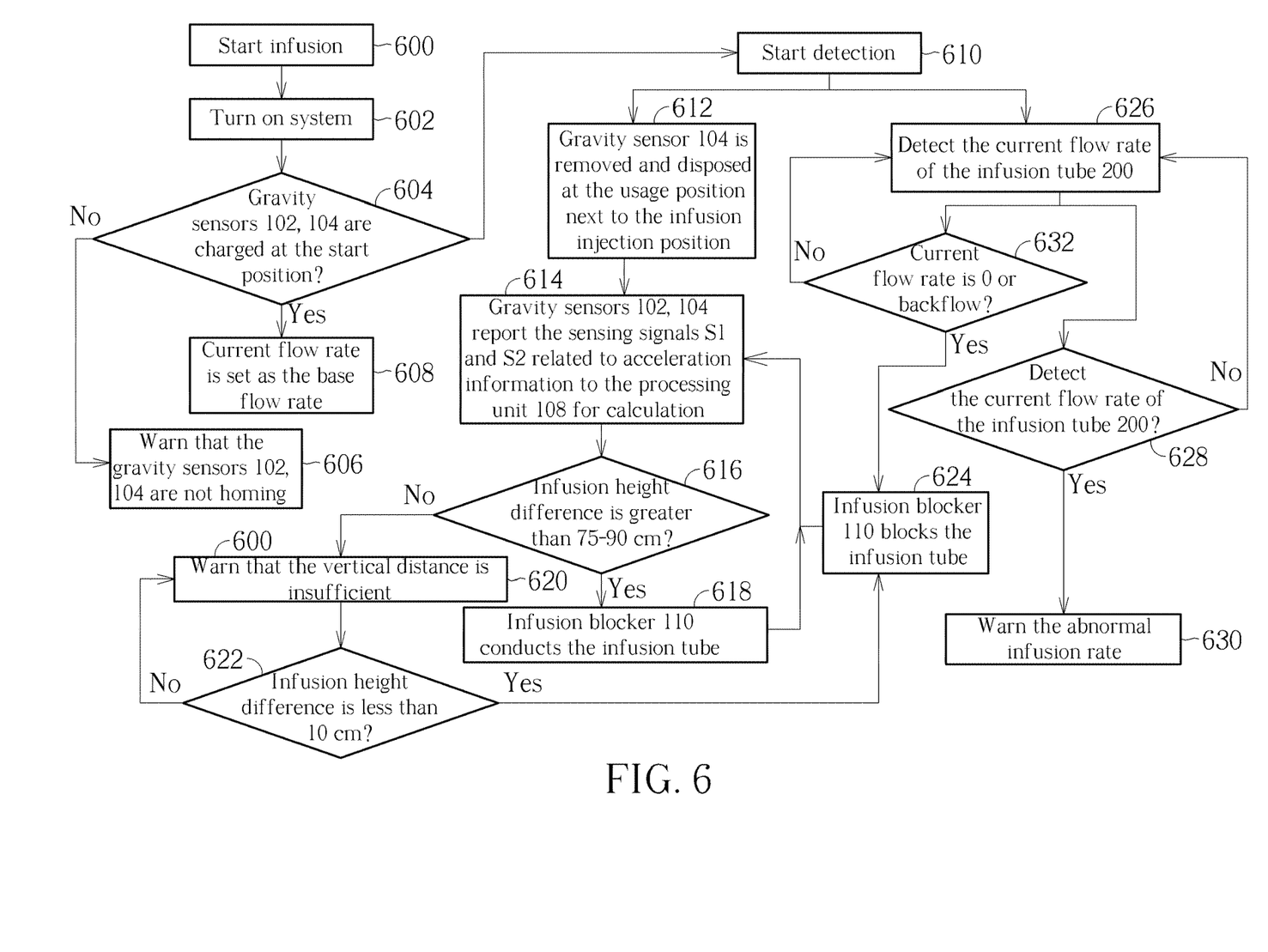
FIG. 6 is a schematic diagram of an infusion height warning and blocking process according to an embodiment of the present invention.

In addition, please refer to FIG. 6, which is a schematic diagram of an infusion height warning and blocking process 60 according to an embodiment of the present invention. As shown in FIG. 6, the nursing staff completes adjustment and starts infusion (step 600), and turns on the infusion height warning and blocking system 10 (step 602). At this moment, the infusion height warning and blocking device 100 detects whether the gravity sensors 102, 104 are charged at the start position (step. 604). If not, the infusion height warning and blocking device 100 warns that the gravity sensors 102, 104 are not homing (step 606); if yes, the current flow rate is set as the base flow rate (step 608). Then infusion height warning and blocking system 10 starts detection (step 610). In terms of height detection, the gravity sensor 104 is removed and disposed at the usage position next to the infusion injection position (step 612). The gravity sensors 102, 104 report the sensing signals S1 and S2 related to acceleration information to the processing unit 108 for calculation (step 614), to determine whether the infusion height difference is greater than 75-90 cm (step 616). If yes, the infusion blocker 110 conducts the infusion tube (step 618); if not, the infusion height warning and blocking device 100 warns that the vertical distance is insufficient (step 620). Afterwards, the processing unit 108 determines whether the infusion height difference is less than 10 cm (step 622). If not, the infusion height warning and blocking device 100 continues to warn is that the vertical distance is insufficient (step 620); if yes, the infusion blocker 110 blocks the infusion tube (step 624).

In terms of flow rate detection, the flow rate sensor 112 continuously detects the current flow rate of the infusion tube 200 (step 626), and the processing unit 108 determines whether the current flow rate is greater than or less than the base flow rate by 25% (step 628). If not, the processing unit 108 continuously detects the current flow rate of the infusion tube 200 (step 626); if yes, the infusion height warning and blocking device 100 warns the abnormal infusion rate (step 630). Further, the processing unit 108 determines whether the current flow rate is 0 or backflow (step 632). If not, the processing unit 108 continuously detects the current flow rate of the infusion tube 200 (step 626); if yes, the infusion blocker 110 blocks the infusion tube (Step 624). For the details of the infusion height warning and blocking process 60, please refer to the above related descriptions, which are not repeated here for brevity.

In addition, the infusion height warning and blocking device 100 may further include a storage unit. The processing unit 108 may be a microprocessor or an application-specific integrated circuit (ASIC). The storage unit may be any data storage device, for storing a program code, and the processing unit 108 reads and executes the program code to complete the above functions and the steps of the infusion height warning and blocking process 60. The storage unit may be subscriber identity module (SIM), read-only memory (ROM), random-access memory (RAM), CD read-only memory (CD-ROM), magnetic tapes, floppy disks, optical data storage devices, etc., but not limited to these.

In summary, the present invention may accurately determine the infusion height difference between the start position and the usage position according to the sensing signals generated by the gravity sensors, and effectively perform different operations for different infusion height differences to maintain a flow rate and avoid a backflow or an excessive flow rate.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An infusion height warning and blocking device, for an infusion stand, the infusion height warning and blocking device comprising:
   a communication module, for receiving at least one sensing signal indicating at least one vertical acceleration from at least one gravity sensor; and
   a processing unit, for calculating an infusion height difference between a start position and a usage position according to the at least one sensing signal, and generating at least one height indication signal according to the infusion height difference and at least one height difference threshold;
   wherein the at least one gravity sensor is disposed at a position related to the usage position, and the usage position is a position of an infusion wearing ring;
   wherein the infusion wearing ring is configured to be worn on an infusion part of a patient;
   wherein the start position is related to an outlet of an infusion bottle disposed on the infusion stand.

2. The infusion height warning and blocking device of claim 1, wherein the processing unit generates a first height indication signal of the at least one height indication signal for warning in response to the infusion height difference being less than a first height difference threshold of the at least one height difference threshold.

3. The infusion height warning and blocking device of claim 2 further comprising an infusion blocker, wherein the processing unit generates a second height indication signal of the at least one height indication signal to instruct the infusion blocker to block an infusion tube in response to the infusion height difference being less than a second height difference threshold of the at least one height difference threshold or greater than a third height difference threshold of the at least one height difference threshold.

4. The infusion height warning and blocking device of claim 1 further comprising a flow sensing device, for detecting a current flow rate of an infusion tube, to generate a flow rate sensing signal, wherein the processing unit generates at least one flow rate indication signal according to the flow rate sensing signal and at least one flow rate threshold.

5. The infusion height warning and blocking device of claim 4, wherein the processing unit generates a first flow rate indication signal of the at least one flow rate indication signal for warning in response to the current flow rate being greater than or less than a first flow rate threshold of the at least one flow rate threshold by a specific ratio; wherein the processing unit generates a second flow rate indication signal of the at least one flow rate indication signal to instruct an infusion blocker to block the infusion tube in response to the current flow rate being less than a second flow rate threshold of the at least one flow rate threshold.

6. The infusion height warning and blocking device of claim 1, wherein the start position is adjustable, a first gravity sensor and a second gravity sensor of the at least one gravity sensor are disposed at the start position and the usage position, and the processing unit calculates the infusion height difference between the start position and the usage position according to a a first sensing signal of the at least one sensing signal generated by the first gravity sensor and a second sensing signal of the at least one sensing signal generated by the second gravity sensor.

7. The infusion height warning and blocking device of claim 1, wherein the start position is fixed, a gravity sensor of the at least one gravity sensor is disposed at the start position first and then disposed at the usage position, and the processing unit calculates the infusion height difference between the start position and the usage position according to a sensing signal of the at least one sensing signal generated by the gravity sensor.

8. The infusion height warning and blocking device of claim 1, wherein the processing unit calculates the infusion height difference between the start position and the usage position according to the at least one vertical acceleration indicated by the at least one sensing signal.

9. The infusion height warning and blocking device of claim 1, wherein the at least one gravity sensor is charged at the start position.

10. The infusion height warning and blocking device of claim 1, wherein the at least one gravity sensor detects acceleration, gravity direction and time to generate the at least one sensing signal.

11. An infusion height warning and blocking method, for an infusion stand, the infusion height warning and blocking method comprising:
    receiving at least one sensing signal indicating at least one vertical acceleration from at least one gravity sensor;
    calculating an infusion height difference between a start position and a usage position according to the at least one sensing signal; and
    generating at least one height indication signal according to the infusion height difference and at least one height difference threshold;
    wherein the at least one gravity sensor is disposed at a position related to the usage position, and the usage position is a position of an infusion wearing ring;
    wherein the infusion wearing ring is configured to be worn on an infusion part of a patient;
    wherein the start position is related to an outlet of an infusion bottle disposed on the infusion stand.

12. The infusion height warning and blocking method of claim 11 further comprising:
    in response to the infusion height difference being less than a first height difference threshold of the at least one height difference threshold, generating a first height indication signal of the at least one height indication signal for warning.

13. The infusion height warning and blocking method of claim 12 further comprising:
in response to the infusion height difference being less than a second height difference threshold of the at least one height difference threshold or greater than a third height difference threshold of the at least one height difference threshold, generating a second height indication signal of the at least one height indication signal to block an infusion tube.

14. The infusion height warning and blocking method of claim 11 further comprising:
detecting a current flow rate of an infusion tube, to generate a flow rate sensing signal; and
generating at least one flow rate indication signal according to the flow rate sensing signal and at least one flow rate threshold.

15. The infusion height warning and blocking method of claim 14 further comprising:
in response to the current flow rate being greater than or less than a first flow rate threshold of the at least one flow rate threshold by a specific ratio, generating a first flow rate indication signal of the at least one flow rate indication signal for warning; and
in response to the current flow rate being less than a second flow rate threshold of the at least one flow rate threshold, generating a second flow rate indication signal of the at least one flow rate indication signal to block the infusion tube.

16. The infusion height warning and blocking method of claim 11, wherein the start position is adjustable, a first gravity sensor and a second gravity sensor of the at least one gravity sensor are disposed at the start position and the usage position, the infusion height warning and blocking method further comprises:
calculating the infusion height difference between the start position and the usage position according to a first sensing signal of the at least one sensing signal generated by the first gravity sensor and a second sensing signal of the at least one sensing signal generated by the second gravity sensor.

17. The infusion height warning and blocking method of claim 11, wherein the start position is fixed, a gravity sensor of the at least one gravity sensor is disposed at the start position first and then disposed at the usage position, and the infusion height warning and blocking method further comprises:
calculating the infusion height difference between the start position and the usage position according to a sensing signal of the at least one sensing signal generated by the gravity sensor.

18. The infusion height warning and blocking method of claim 11 further comprising:
calculating the infusion height difference between the start position and the usage position according to the at least one vertical acceleration indicated by the at least one sensing signal.

19. The infusion height warning and blocking method of claim 11, wherein the at least one gravity sensor is charged at the start position.

20. The infusion height warning and blocking method of claim 11, wherein the at least one sensing signal is generated by detecting acceleration, gravity direction and time.

* * * * *